(12) United States Patent
Hart et al.

(10) Patent No.: US 11,707,313 B2
(45) Date of Patent: Jul. 25, 2023

(54) ELECTROSURGICAL FORCEPS AND METHOD OF MANUFACTURING THE SAME

(71) Applicant: COVIDIEN LP, Mansfield, MA (US)

(72) Inventors: Keir Hart, Lafayette, CO (US); Russell D. Hempstead, Lafayette, CO (US); Edward M. Chojin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1057 days.

(21) Appl. No.: 16/456,282

(22) Filed: Jun. 28, 2019

(65) Prior Publication Data

US 2019/0314078 A1 Oct. 17, 2019

Related U.S. Application Data

(63) Continuation of application No. 15/018,557, filed on Feb. 8, 2016, now Pat. No. 10,342,597, which is a (Continued)

(51) Int. Cl.
*A61B 18/08* (2006.01)
*A61B 18/14* (2006.01)
*A61B 17/00* (2006.01)

(52) U.S. Cl.
CPC ........ *A61B 18/085* (2013.01); *A61B 18/1445* (2013.01); *A61B 2017/00526* (2013.01); (Continued)

(58) Field of Classification Search
CPC ............ A61B 18/1442; A61B 18/1445; A61B 18/1447; A61B 2018/1442; (Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 Y 9/2009
DE 2415263 A1 10/1975
(Continued)

OTHER PUBLICATIONS

U.S. Appl. No. 08/926,869, filed Sep. 10, 1997, James G. Chandler.
(Continued)

*Primary Examiner* — Joanne M Rodden
*Assistant Examiner* — Nora W Rhodes
(74) *Attorney, Agent, or Firm* — Carter, DeLuca & Farrell LLP

(57) ABSTRACT

A method for manufacturing a jaw assembly configured for use with an electrosurgical forceps is provided. A seal plate with an inwardly facing tab member extending along a peripheral edge thereof is formed. A cavity defined along the inwardly facing tab member of the seal plate is formed. Subsequently, the seal plate is overmolded to a jaw housing. The cavity is configured to receive an insulative substrate therein to facilitate securing the seal plate to the jaw housing.

13 Claims, 3 Drawing Sheets

Related U.S. Application Data continuation of application No. 13/433,924, filed on Mar. 29, 2012, now Pat. No. 9,265,569.

(52) U.S. Cl.
CPC .... *Y10T 29/49002* (2015.01); *Y10T 29/49117* (2015.01); *Y10T 29/49176* (2015.01); *Y10T 29/49208* (2015.01); *Y10T 29/49227* (2015.01); *Y10T 29/49908* (2015.01); *Y10T 29/53257* (2015.01)

(58) Field of Classification Search
CPC ...... A61B 2018/145; A61B 2018/1452; A61B 2018/1455; A61B 2018/1457; A61B 2018/146; A61B 2018/1462
See application file for complete search history.

(56) References Cited

U.S. PATENT DOCUMENTS

| | | |
|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| 5,868,761 A * | 2/1999 | Nicholas ............ A61B 17/1285 606/139 |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| 6,908,463 B2 | 6/2005 | Treat et al. |
| D509,297 S | 9/2005 | Wells |
| D525,361 S | 7/2006 | Hushka |
| D531,311 S | 10/2006 | Guerra et al. |
| 7,135,020 B2 | 11/2006 | Lawes et al. |
| D533,274 S | 12/2006 | Visconti et al. |
| D533,942 S | 12/2006 | Kerr et al. |
| 7,147,638 B2 | 12/2006 | Chapman et al. |
| D535,027 S | 1/2007 | James et al. |
| 7,160,299 B2 | 1/2007 | Baily |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| 7,396,265 B2 | 7/2008 | Darley et al. |
| 7,396,356 B2 | 7/2008 | Mollenauer |
| D575,395 S | 8/2008 | Hushka |
| D575,401 S | 8/2008 | Hixson et al. |
| 7,442,193 B2 | 10/2008 | Shields et al. |
| D582,038 S | 12/2008 | Swoyer et al. |
| 7,668,597 B2 | 2/2010 | Engmark et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,877,853 B2 | 2/2011 | Unger et al. |
| D649,249 S | 11/2011 | Guerra |
| D649,643 S | 11/2011 | Allen, IV et al. |
| 8,112,871 B2 | 2/2012 | Brandt et al. |
| 8,469,716 B2 | 6/2013 | Fedotov et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,898,888 B2 | 12/2014 | Brandt et al. |
| 8,900,232 B2 | 12/2014 | Ourada |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,513 B2 | 2/2015 | Allen, IV et al. |
| 8,961,515 B2 | 2/2015 | Twomey et al. |
| 8,968,283 B2 | 3/2015 | Kharin |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,316 B2 | 3/2015 | Roy et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,484 B2 | 5/2015 | Craig |
| 9,028,492 B2 | 5/2015 | Kerr et al. |
| 9,039,704 B2 | 5/2015 | Joseph |
| 9,039,732 B2 | 5/2015 | Sims et al. |
| 9,060,780 B2 | 6/2015 | Twomey et al. |
| 9,113,882 B2 | 8/2015 | Twomey et al. |
| 9,113,899 B2 | 8/2015 | Garrison et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,113,940 B2 | 8/2015 | Twomey |
| 9,161,807 B2 | 10/2015 | Garrison |
| 9,259,268 B2 | 2/2016 | Behnke, II et al. |
| 9,265,565 B2 | 2/2016 | Kerr |
| 9,265,568 B2 | 2/2016 | Chernov et al. |
| 9,265,569 B2 | 2/2016 | Hart et al. |
| 9,314,295 B2 | 4/2016 | Garrison |
| 9,333,002 B2 | 5/2016 | Garrison |
| 9,381,059 B2 | 7/2016 | Garrison |
| 9,456,870 B2 | 10/2016 | Chernov et al. |

(56) References Cited

U.S. PATENT DOCUMENTS

| | | | |
|---|---|---|---|
| 9,486,220 B2 | 11/2016 | Twomey et al. | |
| 9,492,221 B2 | 11/2016 | Garrison | |
| 9,615,877 B2 | 4/2017 | Tyrrell et al. | |
| 9,636,169 B2 | 5/2017 | Allen, IV et al. | |
| 9,668,806 B2 | 6/2017 | Unger et al. | |
| 9,693,816 B2 | 7/2017 | Orszulak | |
| 9,844,384 B2 | 12/2017 | Chernov et al. | |
| 10,045,811 B2 | 8/2018 | Sharp et al. | |
| 10,117,705 B2 | 11/2018 | Chernov et al. | |
| 10,342,597 B2* | 7/2019 | Hart | A61B 18/1445 |
| 2003/0216733 A1 | 11/2003 | McClurken et al. | |
| 2005/0021026 A1 | 1/2005 | Baily | |
| 2006/0141861 A1 | 6/2006 | Darley et al. | |
| 2008/0058802 A1* | 3/2008 | Couture | A61B 18/1442 606/51 |
| 2008/0195093 A1* | 8/2008 | Couture | A61B 18/1445 606/45 |
| 2008/0208289 A1 | 8/2008 | Darley et al. | |
| 2009/0082766 A1* | 3/2009 | Unger | A61B 18/1445 606/51 |
| 2009/0082769 A1 | 3/2009 | Unger et al. | |
| 2009/0216229 A1 | 8/2009 | Chojin | |
| 2010/0179543 A1 | 7/2010 | Johnson et al. | |
| 2010/0204697 A1 | 8/2010 | Dumbauld et al. | |
| 2010/0204698 A1 | 8/2010 | Chapman et al. | |
| 2012/0083784 A1* | 4/2012 | Davison | A61B 18/1445 606/41 |
| 2012/0123404 A1 | 5/2012 | Craig | |
| 2012/0172868 A1 | 7/2012 | Twomey et al. | |
| 2012/0239034 A1 | 9/2012 | Horner et al. | |
| 2012/0265241 A1 | 10/2012 | Hart et al. | |
| 2012/0296238 A1 | 11/2012 | Chernov et al. | |
| 2012/0330308 A1 | 12/2012 | Joseph | |
| 2013/0022495 A1 | 1/2013 | Allen, IV et al. | |
| 2013/0071282 A1 | 3/2013 | Fry | |
| 2013/0079774 A1 | 3/2013 | Whitney et al. | |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10045375 A1 | 4/2002 |
| DE | 202007009165 U1 | 8/2007 |
| DE | 202007009317 U1 | 8/2007 |
| DE | 202007016233 U1 | 1/2008 |
| DE | 102004026179 B4 | 1/2009 |
| DE | 102008018406 B3 | 7/2009 |
| EP | 1159926 A2 | 3/2003 |
| JP | 61501068 A | 5/1986 |
| JP | 1024051 | 1/1989 |
| JP | 1147150 | 6/1989 |
| JP | 55106 | 1/1993 |
| JP | 0540112 A | 2/1993 |
| JP | 6121797 | 5/1994 |
| JP | 6285078 A | 10/1994 |
| JP | 06343644 | 12/1994 |
| JP | 6511401 A | 12/1994 |
| JP | 07265328 | 10/1995 |
| JP | 856955 | 5/1996 |
| JP | 08252263 A | 10/1996 |
| JP | 8289895 A | 11/1996 |
| JP | 8317934 A | 12/1996 |
| JP | 8317936 A | 12/1996 |
| JP | 910223 A | 1/1997 |
| JP | 9122138 A | 5/1997 |
| JP | 10155798 A | 6/1998 |
| JP | 11070124 A | 3/1999 |
| JP | 11169381 A | 6/1999 |
| JP | 11192238 A | 7/1999 |
| JP | 11244298 | 9/1999 |
| JP | 2000102545 A | 4/2000 |
| JP | 2000342599 A | 12/2000 |
| JP | 2000350732 A | 12/2000 |
| JP | 2001003400 A | 1/2001 |
| JP | 2001008944 | 1/2001 |
| JP | 2001029356 | 2/2001 |
| JP | 2001128990 A | 5/2001 |
| JP | 2001190564 A | 7/2001 |
| JP | 2002528166 A | 9/2002 |
| JP | 2003245285 A | 9/2003 |
| JP | 2004517668 A | 6/2004 |
| JP | 2004528869 A | 9/2004 |
| JP | 2011125195 A | 6/2011 |
| JP | 0006030945 B2 | 11/2016 |
| JP | 6502328 B2 | 4/2019 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 2005110264 A2 | 4/2006 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
Michael Choti, "Abdominoperineal Resection with the LigaSure Vessel Sealing System and LigaSure Atlas 20 cm Open Instrument" Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Chariotte,NC; Date: Aug. 2003.
Peterson et al., "Comparison of Healing Process Following Ligation with Sutures and Bipolar Vessel Sealing" Surgical Technology International (2001).
"Electrosurgery: A Historical Overview" Innovations in Electrosurgery; Sales-Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford, "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al. "Extended Left Hemicolectomy Using the LigaSure Vessel Sealing System" Innovations That Work; Sep. 1999.
Kennedy et al. "High-burst-strength, feedback-controlled bipolar vessel sealing" Surgical Endoscopy (1998) 12:876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,Jun. 2002.

(56) References Cited

OTHER PUBLICATIONS

Heniford et al. "Initial Research and Clinical Results with an Electrothermal Bipolar Vessel Sealer" Oct. 1999.
Heniford et al "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery"; Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 10672.9 dated Oct. 16, 2007.
Int'l Search Report EP 07 13779.9 dated Oct. 26, 2007.
Int'l Search Report EP 07 14016 dated Jan. 28, 2008.
Int'l Search Report EP 07 15191.5 dated Jan. 23, 2008.
Int'l Search Report EP 07 15601.3 dated Jan. 4, 2008.
Int'l Search Report EP 07 16911 dated May 28, 2010.
Int'l Search Report Ep 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 16539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 10521.4 dated Dec. 16, 2009.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.

(56) References Cited

OTHER PUBLICATIONS

Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 09 11745.8 dated Jan. 5, 2010.
Int'l Search Report EP 09 12629.3 dated Dec. 8, 2009.
Int'l Search Report EP 09 12687.1 dated Dec. 23, 2009.
Int'l Search Report EP 09 12688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 11750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10.169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report Ep 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.

* cited by examiner

ELECTROSURGICAL FORCEPS AND METHOD OF MANUFACTURING THE SAME

CROSS-REFERENCE TO RELATED APPLICATIONS

The present application is a continuation application of U.S. patent application Ser. No. 15/018,557, filed on Feb. 8, 2016, which is a continuation application of U.S. patent application Ser. No. 13/433,924, filed on Mar. 29, 2012, now U.S. Pat. No. 9,265,569, the entire contents of which are incorporated herein by reference.

BACKGROUND

Technical Field

The present disclosure relates to an electrosurgical forceps and, more particularly, to a method of manufacturing an end effector assembly including jaw members with seal plates having inwardly facing tab members formed thereon to facilitate overmolding the seal plates to respective jaw housings of the jaw members.

Description of Related Art

Electrosurgical forceps are well known in the medical arts. For example, an electrosurgical endoscopic forceps is utilized in surgical procedures, e.g., laparoscopic surgical procedure, where access to tissue is accomplished through a cannula or other suitable device positioned in an opening on a patient. The endoscopic forceps, typically, includes a housing, a handle assembly including a movable handle, a drive assembly, a shaft and an end effector assembly attached to a distal end of the shaft. Typically, the endoscopic forceps utilizes both mechanical clamping action and electrical energy to effect hemostasis by heating the tissue and blood vessels to coagulate, cauterize, seal, cut, desiccate, and/or fulgurate tissue. In particular, the jaw members operably communicate with the drive assembly to manipulate tissue, e.g., grasp and seal tissue and the jaw members have respective seal plates secured to the jaw housing of the respective jaw members to seal tissue.

As is conventional in the endoscopic forceps art, the seal plates are, typically, secured to the respective jaw housing of the respective jaw members via an overmolding process. In particular, a peripheral edge of the seal plate(s) is bent or folded downwards and, subsequently, bent or folded outwards providing a thin lip or tab (referred to in the art as a "pinch trim") that is overmolded to the jaw housing. As can be appreciated, this results in a thin section of the overmolding that may deform at the high temperatures that are typically associated with an electrosurgical procedure, e.g., an electrosurgical sealing procedure. This deformation of the overmolding may lead to delamination of the of the seal plate from the jaw housing. The delamination of the seal plate from the jaw housing may increase the likelihood of flexure of the jaw members and/or seal plates, which, in turn, may increase the likelihood of the seal plates inadvertently coming into contact with one another resulting in arcs developing therebetween.

In addition to the foregoing, one or more wires are typically secured to the seal plates of the respective jaw members to provide electrosurgical energy thereto. In particular, one (in the case of monopolar endoscopic forceps configurations) or two (in the case of bipolar endoscopic forceps configurations) wires are secured to the seal plates on the respective jaw members via a crimping process. This crimping process is complex and increases manufacturing costs of the electrosurgical instrument. Moreover, this crimping process, e.g., a crimp-on terminal that is positioned on one or both of the seal plates and connects to the respective jaw wire, takes up a large amount of space in the relatively limited space of the jaw members.

SUMMARY

In view of the foregoing, there exists a need in the art for a method of manufacturing an end effector assembly including jaw members with seal plates having inwardly facing tab members formed thereon to facilitate overmolding the seal plates to respective jaw housings of the jaw members.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides method for manufacturing a jaw assembly configured for use with an electrosurgical forceps. A seal plate with an inwardly facing tab member extending along a peripheral edge thereof is formed. In certain instances, a jaw wire may be welded to the seal plate. Subsequently, the seal plate is overmolded to a jaw housing. Forming the seal plate may include forming a cavity defined along the inwardly facing tab member of the seal plate. In this instance, the cavity may be configured to receive an insulative substrate therein to facilitate securing the seal plate to the jaw housing.

The insulative substrate may be made from plastic. Forming the seal plate may include forming one or more apertures thereon. In this instance, the aperture(s) is configured to receive the insulative substrate therein such that during the overmolding process of the jaw housing an insulative stop member is formed on the seal plate. The insulative stop member may include a generally arcuate configuration. Forming the seal plate may include forming a plurality of notches along the inwardly facing tab member of the seal plate.

An aspect of the present disclosure provides a method for manufacturing jaw members configured for use with an electrosurgical forceps. One or more of a pair of seal plates is stamped from a sheet metal. The stamped seal plates are formed with an inwardly facing tab member extending along a peripheral edge thereof. In certain instances, a jaw wire may be welded to each of the seal plates. The seal plates are positioned into respective mold cavities. An insulative substrate is introduced into the respective mold cavities. The insulative substrate is allowed to harden in the respective mold cavities to form respective jaw housings with seal plates secured thereto. Forming the seal plates may include forming a cavity defined along the inwardly facing tab member of the seal plate. In this instance, the cavity may be configured to receive the insulative substrate therein to facilitate securing the seal plates to the respective jaw housing. The jaw housings are removed from the respective mold cavities to form a pair of jaw members. The insulative substrate may be made from plastic.

Forming the seal plates may include forming one or more apertures thereon. The aperture(s) may be configured to receive the insulative substrate therein such that during the overmolding process of the respective jaw housing an insulative stop member is formed on the seal plate. The insulative stop member may include a generally arcuate configuration. Forming the seal plates may include forming a plurality of notches along the inwardly facing tab member of the seal plate.

An aspect of the present disclosure provides a method for manufacturing jaw members configured for use with an electrosurgical forceps. A pair of seal plates is stamped from sheet metal. The stamped seal plates may be formed with an inwardly facing tab member extending along a peripheral edge thereof, and one or more apertures thereon. A cavity defined along the inwardly facing tab member of the seal plate is formed. The seal plates are positioned into respective mold cavities. An insulative substrate is introduced into the respective mold cavities. The insulative substrate is allowed to harden in the respective mold cavities to form respective jaw housings with seal plates secured thereto. The cavities are defined along the inwardly facing tab members of the seal plates and are configured to receive the insulative substrate therein to facilitate securing the seal plates to a respective jaw housing. The aperture(s) is configured to receive the insulative substrate therein such that an insulative stop member is formed on the seal plate. The jaw housings is removed from the respective mold cavities to form a pair of jaw members.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
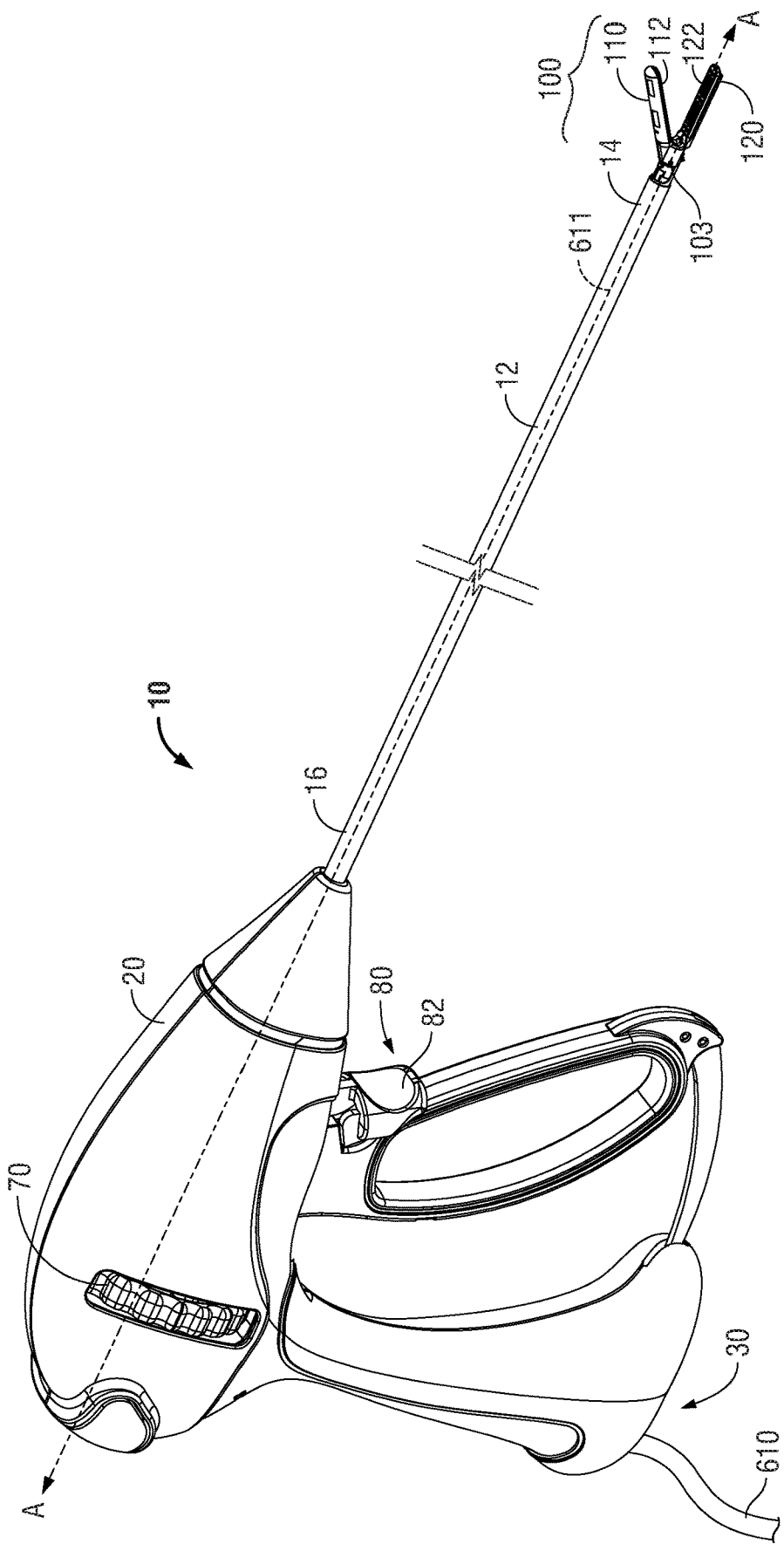
FIG. 1 is a perspective view of an endoscopic electrosurgical forceps utilizing an end effector including jaw members manufactured according to an embodiment of the present disclosure.

Turning now to FIG. 1, an electrosurgical endoscopic forceps 10 (forceps 10) is provided having a longitudinal axis "A-A" defined therethrough, a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source. Alternately, forceps 10 may be configured as a battery powered instrument. Cable 610 includes one or more wires 611 (one wire shown in the drawings) extending therethrough that has sufficient length to extend through shaft 12 in order to provide electrical energy to one or both of the jaw members 110 and 120 of end effector assembly 100.

Continuing with reference to FIG. 1, end effector assembly 100 is designed as a unilateral assembly, e.g., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, e.g., where both jaw member 110 and jaw member 120 are moveable about a pivot 103 relative to one another and to shaft 12. In some embodiments, a knife assembly (not explicitly shown) is disposed within shaft 12 and a knife channel 125 (FIG. 3) is defined within one or both jaw members 110, 120 to permit reciprocation of a knife blade (not explicitly shown) therethrough, e.g., via an activation of trigger 82 (FIG. 1) of trigger assembly 80.

Other than jaw member 110 being movable and jaw member 120 being stationary, jaw members 110 and 120 are identical to one another. In view thereof, and unless otherwise noted, jaw member 120 is described in detail hereinafter.

Figure 2:
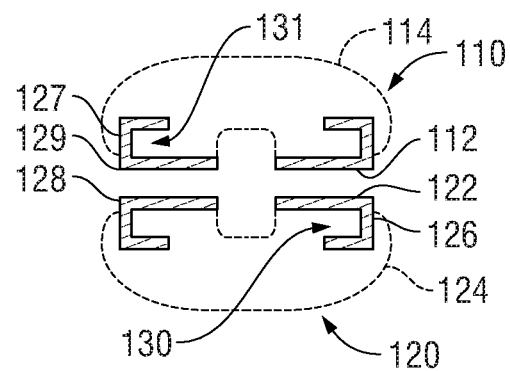
FIG. 2 is a cross-sectional view of a pair of opposing seal plates of the jaw members depicted in FIG. 1 with a corresponding jaw housings illustrated in phantom.

Turning now to FIG. 2, jaw member 120 is illustrated including a jaw housing 124 (shown in phantom). Jaw housing 124 may be made from any suitable material including, but not limited to, plastic (e.g., thermoplastic, thermosetting plastic, etc.), ceramic material, etc. In the illustrated embodiment, jaw housing 124 is made from thermosetting plastic that serves as an insulative substrate, described in more detail below. In certain instances, it may prove advantageous to provide an exterior portion of the jaw housing 124 that is made from metal and an interior portion (e.g., a portion that is configured to support the seal plate 122 thereon) of the jaw housing 124 that made from plastic. In this instance, the interior portion serves as an insulative barrier between the seal plate 122 and the exterior portion of the jaw housing 124.

Continuing with reference to FIG. 2, jaw member 120 includes electrically conductive tissue sealing plate 122. Seal plate 122 may be made via any suitable manufacturing process including a machining process, a stamping process or the like. In the illustrated embodiment seal plate 122 is made via a stamping process and, subsequently, overmolded to jaw housing 124. A stamping or machine press (not shown) may be utilized to cut or "punch" sheet-metal to a desired configuration. Subsequently, the stamping press is utilized to shape the "punched" sheet-metal into one or more suitable configurations by deforming it with a die or other suitable device (not shown). The aforementioned stamping process may include a variety of other sheet-metal manufacturing processes, such as, for example, blanking, embossing, bending, flanging, and coining.

Figure 3:
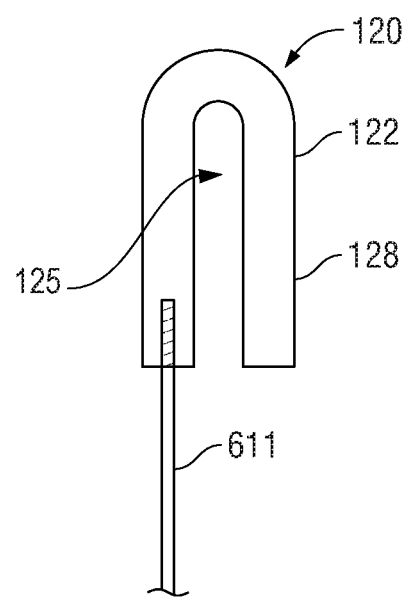
FIG. 3 is a plan view of the lower seal plate depicted in FIG. 2 illustrating a connection point between the seal plate and a jaw wire of the endoscopic electrosurgical forceps.

In accordance with the instant disclosure, the seal plate 122 is formed with an inwardly facing tab member 126 (FIG. 2) that extends along a peripheral edge 128 of the seal plate 122 (FIGS. 2 and 3). Inwardly facing tab member 126 is configured to facilitate securing the seal plate 122 to the jaw housing 124 during a manufacturing process of the jaw member 120. In particular, a cavity or channel 130 (FIG. 2)

is defined along the inwardly facing tab 126 member and is configured to receive the liquid thermosetting plastic therein. More particularly, during manufacture of the jaw member 120, seal plate 122 is positioned within a mold cavity (not explicitly shown) that is configured to support the seal plate 122 therein and shaped to correspond to a desired jaw housing configuration. Subsequently, liquid thermosetting plastic is introduced into the mold cavity to form the jaw housing 124. The cavity 130 of the inwardly facing tab member 126 is configured to receive the liquid thermosetting plastic therein such that when the thermosetting plastic cures, the seal plate 122 firmly secures to the formed jaw housing 124.

The liquid thermosetting plastic may be heated and/or mixed prior to being introduced into the mold cavity. A "single-shot" or "two-shot" injection molding process may be utilized to introduce the liquid thermosetting plastic into the mold cavity.

Jaw member 110 includes an opposing electrically conductive tissue sealing plate 112 including an inwardly facing tab member 127 that extends along a peripheral edge 129 of the seal plate 112 (FIG. 2). Similar to that of cavity 130 of inwardly facing tab member 126, a cavity 131 of the inwardly facing tab member 127 facilitates securing the seal plate 112 to a jaw housing 114 (FIG. 2).

With reference to FIG. 3, wire 611 is operably coupled to the seal plate 122. More particularly, and unlike conventional forceps that utilize a crimping process to couple a jaw wire to a seal plate, wire 611 of the forceps 10 is coupled to the seal plate 122 via a spot welding process, ultrasonic welding process or the like. One of these welding processes e.g., spot welding, is utilized to secure wire 611 to the seal plate 122 prior to the seal plate 122 being positioned within the mold cavity. As can be appreciated, this overcomes the aforementioned drawbacks described above with respect to conventional forceps. That is, the spot welding process is an inexpensive and relatively easy manufacturing method that secures the wire 611 to the seal plate 122, as opposed to the crimping process that typically utilizes crimp-on terminals to secure wires to the seal plates of conventional forceps. The aforementioned spot welding process may be utilized to secure another wire (not explicitly shown) to the seal plate 112.

Figure 4:
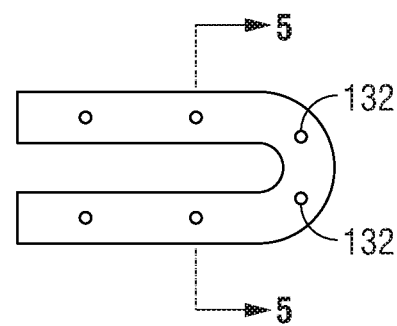
FIG. 4 a plan view of a seal plate configured for use with the jaw members depicted in FIG. 1 according to an embodiment of the present disclosure.
Figure 5:
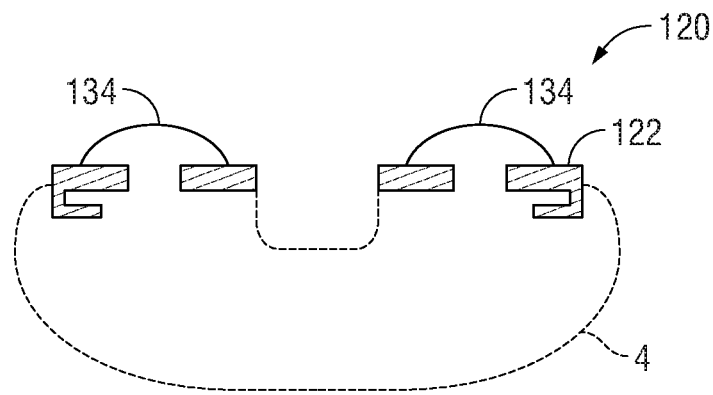
FIG. 5 is a cross-sectional view of the seal plate depicted in FIG. 4 taken along line segment 5-5 with the corresponding jaw housing illustrated in phantom.

In embodiments, it may prove advantageous to provide one or more insulative or non-conductive stop members on one or both of the seal plates 112 and 122. In accordance with the present disclosure, either of seal plates 112 or 122 may be formed with one or more apertures 132 of suitable configuration (FIG. 4). For illustrative purposes, six (6) apertures 132 are shown formed on seal plate 122. Apertures 132 are configured to receive the liquid thermosetting plastic therein such that during the manufacturing process of the jaw housing 124, an insulative stop member(s) 134 forms on the seal plate 122 of the jaw member 120 (FIG. 5). In particular, during the molding process of the jaw housing 124, the liquefied thermosetting plastic seeps or flows through the apertures 132 and cures on a seal surface of the seal plate 122 as the jaw housing 124 cures. In the illustrated embodiment, the cured stop members 134 include a generally arcuate configuration having a dimple or mushroom like profile (as best see in FIG. 5), although other configurations are contemplated.

The stop members 134 function similar to that of stop members that are typically associated with conventional forceps. That is, the stop members 134 may provide a specific gap distance between the jaw members 110 and 120 when the jaw members 110 and 120 are in the clamping configuration. Moreover, the stop members 134 may function to prevent the seal plates 112 and 122 from touching one another during the transmission of electrosurgical energy to the jaw members 110 and 120. In embodiments, the gap distance may range from about 0.001 inches to about 0.0016 inches. Unlike conventional stop members that are typically glued to seal plates via one or more suitable adhesives, and which are prone to becoming dislodged from the seal plates under high shear forces, the stop members 134 of the instant disclosure are formed with the jaw housing 124 and, thus, are permanently affixed to the seal surface of the seal plate 122. Therefore, the likelihood of the stop members 134 becoming dislodged from the seal surface of the seal plate 124 is diminished, if not eliminated.

In embodiment, where each of the seal plates 112 and 122 includes stop members 134, the stop members 134 on the seal plates 112 and 122 may be in vertical registration with one another.

In certain embodiments, after the jaw housing 124 and/or stop members 134 have cured, a buffing machine or the like may be utilized to smooth out rough edges that may have formed during the curing process.

In use, tissue may be positioned between the jaw members 110 and 120. Subsequently, electrosurgical energy is transmitted to the seal plates 112 and 122 via wires 611. The unique configuration of the seal plates 112, 122 including the respective inwardly facing tab members 127, 126 associated therewith overcome the aforementioned drawbacks typically associated with conventional forceps. That is, the inwardly facing tab members 127, 126 including the respective cavities 131, 130 defined therein provides a greater point of contact between the jaw housings 114, 124 and seal plates 112, 122, and, thus, the likelihood of the seal plates 112, 122 delaminating adjacent the point of contact between the seal plates 112, 122 and jaw housings 114, 124 is diminished, if not eliminated.

From the foregoing and with reference to the various figure drawings, those skilled in the art will appreciate that certain modifications can also be made to the present disclosure without departing from the scope of the same. For example, in certain instances, it may prove advantageous to secure the seal plates 112 and 122 to the respective jaw housing 114, 124 of the jaw members 110 and 120 via a different securement method.

Figure 6:
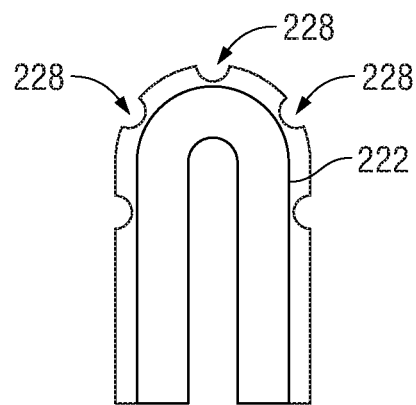
FIG. 6 is a plan view of a seal plate configured for use with the jaw members depicted in FIG. 1 according to another embodiment of the present disclosure.

With reference to FIG. 6 a plan view of a seal plate according to an alternate embodiment is shown designated as a seal plate 222. Seal plate 222 is similar to that of seal plate 122, however, unlike seal plate 122 that includes an inwardly facing tab member 126, seal plate 222 includes an outwardly facing tab member 226. Unlike conventional seal plates that utilize outwardly facing tab members, outwardly facing tab member 226 includes one or more notches 228. Notches 228 allow for local, thicker wall section (not explicitly shown) that adds strength to the jaw housing (not explicitly shown). As with the cavity 130 defined in the inwardly facing tab member 126, the notches 228 of the outwardly facing tab member 226 are configured to receive the liquid thermosetting plastic therein. When the liquid thermosetting plastic cures, the seal plate 222 is firmly secured to the jaw housing.

The unique configuration of the seal plate 222 including the outwardly facing tab member 226 associated therewith overcomes the aforementioned drawbacks typically associated with conventional forceps. That is, the outwardly facing tab member 226 including the notches 228 defined therein provide a greater point of contact between the jaw housing and seal plate 222, and, thus, the likelihood of the seal plate 222 delaminating adjacent the point of contact between the seal plate 222 and jaw housing is diminished, if not eliminated.

In another embodiment, one or both of the inwardly facing tab members 126, 127 may include one or more of the notches 228 thereon.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A jaw member configured for use with an electrosurgical forceps, the jaw member comprising:
    a seal plate including:
        a top surface defining a knife channel extending along a longitudinal axis thereof; and
        a tab extending along a peripheral edge of the seal plate from the top surface and having a first portion and a second portion, the first portion extending substantially perpendicular to, and away from, the top surface and the second portion extending from the first portion toward the knife channel and substantially parallel to the top surface to define a cavity between an inner surface of the first portion, an upper surface of the second portion, and a bottom side of the top surface; and
    an overmolding material secured to the seal plate and surrounding the second portion.

2. The jaw member according to claim 1, further comprising a wire electrically coupled to the seal plate, the wire configured to transmit electrosurgical energy to the seal plate.

3. The jaw member according to claim 1, further comprising a jaw housing operably coupled to the seal plate, wherein a portion of the jaw housing is disposed within the cavity.

4. The jaw member according to claim 1, wherein the seal plate defines at least one aperture extending through the top surface thereof.

5. The jaw member according to claim 4, further comprising an insulative material disposed within the at least one aperture.

6. The jaw member according to claim 4, further comprising a non-insulative material disposed within the at least one aperture.

7. The jaw member according to claim 1, further comprising a stop member disposed on the top surface of the seal plate.

8. The jaw member according to claim 7, wherein the stop member is formed of an insulative material.

9. The jaw member according to claim 1, further comprising a jaw housing operably coupled to the seal plate and wherein at least a portion of the tab includes at least one notch defined therein and configured to provide an enhanced point of contact between the seal plate and the jaw housing.

10. The jaw member according to claim 1, wherein the tab extends along an outer peripheral edge of the seal plate.

11. The jaw member according to claim 1, wherein the top surface faces an opposing seal plate of an opposing jaw member of the electrosurgical forceps.

12. The jaw member according to claim 1, wherein a portion of the overmolding material is disposed within the cavity.

13. The jaw member according to claim 12, wherein the overmolding material is insulative.

* * * * *